US008609693B2

(12) United States Patent
Erickson-Miller et al.

(10) Patent No.: US 8,609,693 B2
(45) Date of Patent: Dec. 17, 2013

(54) METHODS OF ADMINISTRATION OF THROMBOPOIETIN AGONIST COMPOUNDS

(75) Inventors: Connie L. Erickson-Miller, Collegeville, PA (US); Julian Jenkins, King of Prussia, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 13/321,577

(22) PCT Filed: May 27, 2010

(86) PCT No.: PCT/US2010/036294
§ 371 (c)(1),
(2), (4) Date: Nov. 21, 2011

(87) PCT Pub. No.: WO2010/138656
PCT Pub. Date: Dec. 2, 2010

(65) Prior Publication Data
US 2012/0064036 A1 Mar. 15, 2012

Related U.S. Application Data

(60) Provisional application No. 61/182,148, filed on May 29, 2009.

(51) Int. Cl.
*A61K 31/4152* (2006.01)

(52) U.S. Cl.
USPC ......... 514/317; 514/14.9; 514/12.2; 514/404; 514/13.5

(58) Field of Classification Search
USPC ............ 514/404, 12.2, 13.5, 14.9, 317; 435/2
See application file for complete search history.

(56) References Cited

U.S. PATENT DOCUMENTS

| | | | |
|---|---|---|---|
| 851,444 A | 4/1907 | Shulthess | |
| 2,809,963 A | 10/1957 | Hanhart | 534/665 |
| 2,950,273 A | 8/1960 | Pelz | |
| 3,366,619 A | 1/1968 | DeLucia | |
| 4,435,417 A | 3/1984 | Toja et al. | |
| 4,510,149 A | 4/1985 | Cozzi et al. | |
| 4,582,831 A | 4/1986 | Robertson | |
| 4,686,285 A | 8/1987 | Pedrazzi | 534/606 |
| 4,880,788 A | 11/1989 | Moake et al. | |
| 4,948,900 A | 8/1990 | Iijima et al. | |
| 5,326,776 A | 7/1994 | Winn et al. | |
| 5,482,546 A | 1/1996 | Eida et al. | |
| 5,532,202 A | 7/1996 | Yoshida | |
| 5,622,818 A | 4/1997 | Kapp et al. | |
| 5,669,967 A | 9/1997 | Hays | |
| 5,746,821 A | 5/1998 | Hays | |
| 5,760,038 A | 6/1998 | Murugesan et al. | |
| 5,766,581 A | 6/1998 | Bartley et al. | |
| 5,932,546 A | 8/1999 | Barrett et al. | |
| 6,214,813 B1 | 4/2001 | Zhang et al. | |
| 6,238,442 B1 | 5/2001 | Schumacher et al. | |
| 6,248,871 B1 | 6/2001 | Ebenezer et al. | |
| 6,280,959 B1 | 8/2001 | Gleason et al. | |
| 6,436,915 B1 | 8/2002 | Zhang et al. | |
| 2003/0060453 A1 | 3/2003 | Zhang et al. | |
| 2004/0019190 A1 | 1/2004 | Erickson-Miller et al. | |
| 2004/0063764 A1 | 4/2004 | Takemoto et al. | |
| 2004/0082626 A1 | 4/2004 | Takemoto et al. | |
| 2009/0304634 A1 | 12/2009 | Erickson-Miller et al. | |
| 2010/0040683 A1 | 2/2010 | Muller et al. | |
| 2010/0075928 A1 | 3/2010 | Erickson-Miller et al. | |

FOREIGN PATENT DOCUMENTS

| | | |
|---|---|---|
| DE | 193350 | 11/1904 |
| DE | 193350 | 12/1907 |
| DE | 1046220 | 12/1958 |
| EP | 0 638 617 | 4/1994 |
| EP | 1 207 155 | 7/2000 |
| EP | 1 253 142 | 1/2001 |
| EP | 1 104 674 | 6/2001 |
| GB | 826207 | 7/1956 |
| GB | 779 880 | 7/1957 |
| JP | 2002-371213 | 12/2002 |
| WO | WO 93/17681 | 9/1993 |
| WO | WO 94/26709 | 11/1994 |
| WO | WO 96/40750 | 12/1996 |
| WO | WO 98/46606 | 10/1998 |
| WO | WO 99/15500 | 1/1999 |
| WO | WO 99/11262 | 11/1999 |
| WO | WO 00/35446 | 6/2000 |
| WO | WO 00/68222 | 11/2000 |
| WO | WO 01/77080 | 1/2001 |
| WO | WO 01/07423 | 2/2001 |
| WO | WO 01/17349 | 3/2001 |

(Continued)

OTHER PUBLICATIONS

Promacta product insert (2008, downloaded from the internet on Oct. 2, 2012, URL: http://web.archive.org/web/20081203002456/http://us.gsk.com/products/assets/us_promacta.pdf.*
Bussel, et al., Blood, 110(11):391A XP009164945 (2007).
Dmytrijuk, et al., Oncology, 23(13):1171-1177 (2009).
Cwirla, S.E., et al., Science, 276:1696 (1997).
Yamazaki, et al., Database HCAPLUS, AN 1995: Abstract, 196968.
A. Esteve, Ann. Pharm. Franc., 1950, vol. 8, No. 9-10, pp. 594-604.
Morris, et al., Anti-Cancer Drugs, 1997, vol. 8, No. 8, pp. 746-755.
Duffy, et al., J. Med. Chem., 2001, vol. 44, No. 22, Abstract No. XP002197261.
Bartley, et al., Cell, 1994, vol. 77, pp. 1117-1124.
Olszewski, et al., Database CAPLUS on STN, 1995, Chem. Abstracts, No. 122:81695.
Olszewski, et al., J. Org. Chem., 1994, vol. 59, pp. 4285-4296.
Lamb, et al., Nucleic Acids Research, 1995, vol. 23, No. 16, pp. 3283-3289.

(Continued)

*Primary Examiner* — Savitha Rao
(74) *Attorney, Agent, or Firm* — Wayne J. Dustman; Edward R. Gimmi

(57) ABSTRACT

The embodiments provide methods of administering a high dose or a loading dose of a TPO modulator to a subject. The embodiments further provide methods of treating thrombocytopenia and/or neutropenia in a subject. Additionally, the embodiments further provide methods of increasing platelet production and/or enhancing the number of peripheral blood stem cells in a subject.

13 Claims, No Drawings

(56) References Cited

FOREIGN PATENT DOCUMENTS

| WO | WO 01/21180 | 3/2001 |
|---|---|---|
| WO | WO 01/34585 | 5/2001 |
| WO | WO 01/77108 | 10/2001 |
| WO | WO01/89457 | 11/2001 |
| WO | WO 02/59099 | 1/2002 |
| WO | WO 02/59100 | 1/2002 |
| WO | WO 02/49413 | 6/2002 |
| WO | WO 02/057300 | 7/2002 |
| WO | WO 02/085343 | 10/2002 |
| WO | WO 03/045379 | 5/2003 |
| WO | WO03/074550 | 9/2003 |
| WO | WO03/098992 | 12/2003 |
| WO | WO 03/103686 | 12/2003 |
| WO | WO2004029049 A1 | 4/2004 |
| WO | WO 2004/054515 | 7/2004 |
| WO | WO 2004/096154 | 11/2004 |
| WO | WO 2005/041867 | 12/2005 |
| WO | WO2008/101141 | 8/2008 |
| WO | WO2008/136843 | 11/2008 |
| WO | WO2009/151862 | 12/2009 |
| WO | WO2010/045310 | 4/2010 |
| WO | WO2010/129738 | 11/2010 |
| WO | WO2010/138656 | 11/2010 |

OTHER PUBLICATIONS

Seidel, et al., Proc. Natl. Acad. Sci. USA, Mar. 1995, vol. 92, pp. 3041-3045.
Berkhout, et al., J. of Biological Chemistry, Jun. 1997, vol. 272, No. 26, pp. 16404-16413.
Vermeulen, et al., Blood, 1998, vol. 92, No. 3, pp. 894-900.
Hasegawa, et al., Int. J. Immunopharmac, 1996, vol. 18, No. 2, pp. 103-112.
Kumamoto, et al., British Journal of Haematology, 1999, vol. 105, pp. 1025-1033.
Komatsu, et al., Blood, 1996, vol. 87, No. 11, pp. 4552-4560.
Uguccioni, et al., J. Exp. Med., 1996, vol. 183, pp. 2397-2384.
Taylor, et al., J. Org. Chem., 1987, vol. 52, pp. 4107-4110.
Ballestrero, et al., Oncology, 2000, vol. 59, pp. 7-13.
Sawai, et al., Journal of Leukocyte Biology, Jul. 2000, vol. 68, pp. 137-143.
Bussel, et al., Seminars in Hematology, 2000, vol. 37, pp. 1-49 (Table of Contents).
McDonald, et al., Am. J. of Pediatric Hematology/Oncology, 1992, vol. 14, No. 1, pp. 8-21.
Souyri, et al., Cell, 1990, vol. 63, pp. 1137-1147.
Bazan, et al., Pro. Natl. Acad. Sci. USA, Sep. 1990, vol. 87, pp. 6934-6938.
Kaushansky, et al., Nature, Jun. 16, 1994, vol. 369, pp. 568-571.
King, et al., The Journal of Immunology, 2000, pp. 3774-3782.
Kikuta, et al., Experimental Hematology, 2000, vol. 28, pp. 311-317.
Somlo, et al., Blood, May 1, 1992, vol. 93, No. 9, pp. 2798-2806.
Kirley-Neumann, et al., Cytokines, Cellular & Molecular Therapy, 2000, vol. 6, pp. 47-56.
Egger, et al., Bone Marrow Transplant, 1998, vol. 22, pp. 34-35.
Gaudron, et al., Stem Cells, 1999, vol. 17, pp. 100-106.
Fetscher, et al., Current Opinion in Hematology, 2000, vol. 7, pp. 255-260.
Clemons, et al., Breast Cancer Res. Treatment, 1999, vol. 57, pp. 127.
Greene, "Protective Groups in Organic Synthesis", 1981, Table of Contents.
Methia, et al., Blood, 1993, vol. 82, No. 5, pp. 1395-1401.
Yamazaki, et al., Japn. J. Toxicol. Environ. Health, 1994, vol. 94, No. 5, pp. 448-453.
Duffin, et al., J. of the Chem. Soc., 1954, pp. 408-441.
King, et al., Scand. J. of Immunol., 1999, vol. 49, No. 2, pp. 184-192.
Konica Corp. Derwent No. 92-077508/10, 1992.
Mitsubishi Pharma Corp. Derwent No. 2003-845201/78, 2003.
Mitsubishi Pharma Corp. Derwent No. 2003-767492/72, 2003.
Balli, et al., Dyes. Pigm., 1981, vol. 2, No. 2, pp. 93-124.
Balli, et al., Justus Liebigs Ann. Chem., 1966, vol. 699, pp. 133-134.
Dziomko, et al., Chem. Heterocycl. Compd., 1984, vol. 20, No. 2, pp. 196-200.
Duffy, et al., J. Med. Chem., 2001, vol. 44, No. 22, p. 3730-3745.
Kimura, et al., FEBS Letters, 1998, vol. 428, No. 3, pp. 250-254.
Beckert, et al., Monatshefte Fur Chemie, 1989, vol. 120, pp. 1125-1137.
A. Esteve, Ann. Pharm. Franc., 1950, vol. 8, No. 9-10.
Minssen-Guette, et al., Bulletin De La Societe Chimique De France, 1986, No. 5, pp. 2106-2110.
European Search report dated Dec. 15, 2003.
European office action dated Feb. 2, 2005.
Bussel, et al., Seminars in Hematology, 2000, vol. 37, pp. 1-49 (whole journal). see ids #7.
Balli, et al., Dyes. Pigm., 1981, vol. 2, No. 2, pp. 93-124 (sent original).
Balli, et al., Justus Liebigs Ann. Chem., 1966, vol. 699, pp. 133-144. (sent original).
Maler, et al., *Molecular Psychiatry*, 11 :1113-1115 (2006).
Small, et al., *Proc. Natl. Acad. Sci.*, 91:459-463 (1994).
Tsai, et al., *Journal of Experimental Medicine*, 204(6):1273-1280 (2007).
Wu, et al., *Pathobiology*, 75:186-194 (2008).
*ClinicalTrials.gov*, SB497115 (Oral Thrombopoietin Receptor Agonist) Versus Placebo in Adults with Thrombocytopenia Due to Hepatitis C, Study Completion: May 13, 2005.
People's Republic of China, Office Action, dated Mar. 17, 2006.
Asco Poster, Jun. 2006.
Basser et al., *Blood*, 89:3118-3128 (1997).
Fanucchi et al., *New Engl. J. Medicine*, 336:404-409 (1997).
Hasegawa, et al., *Int. J. Immunopharmac*, 18(2):103-112 (1996).
Kuter et al., *Proc. Natl. Acad. Sci.*, 91:11104-11108 (1994).
Kuter, Iet al., *The Oncologist*, 1:98-106 (1996).
Kuter, et al., *Seminars in Hematology*, 37(2):41-49 (2000).
Laurenz, et al., *Comp. Biochem Physiol.*, 116A(4):369-377 (1997).
Lok, et al., *Nature*, 369:565-568 (1994).
Metcalf, et al., *Nature*, 369:519-520 (1994).
RXLIST, *Promacta Drug Description*, online article, http://www.rxlist.com/promacta-drug.htm;, p. 1, para 4; p. 2, para 1, 6, 9; p. 12, para 4 (Jul. 8, 2010).
Sauvage, et al., *Nature*, 369:533-538 (1994).
Shiotsu, et al., *Experimental Hematology*, 26:1195-1201 (1998).
Vigon, et al., *Proc. Natl. Acad. Sci. USA*, 89:5640-5644 (1992).
Wendling, et al., *Nature*, 369:571-574 (1994).
Wendling, et al., *Biotherapy*, 10(4):269-277 (1998).
PCT/US2010/036294 International Search Report, Sep. 17, 2010.

\* cited by examiner

METHODS OF ADMINISTRATION OF THROMBOPOIETIN AGONIST COMPOUNDS

This application is a 371 of International Application No. PCT/US2010/036294, filed 27 May 2010, which claims priority to U.S. Provisional Application 61/182,148 filed 29 May 2009.

BACKGROUND OF THE INVENTION

1. Field of the Invention

The present invention relates to compounds that modulate/activate the human thrombopoietin receptor. Suitably, the method relates to methods of treating thrombocytopenia by administration of 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid or a pharmaceutically acceptable salt thereof, suitably the bis-(monoethanolamine) salt, (hereinafter the bis-(monoethanolamine) salt is Compound A;

which is a compound is represented by Structure I:

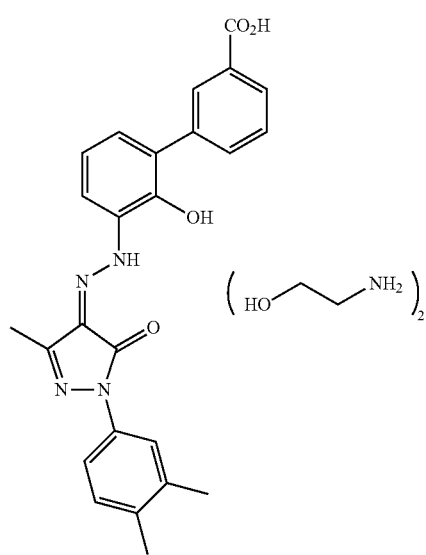

(I)

and Compound B refers to the corresponding salt free compound or a pharmaceutically acceptable salt thereof).

2. Description of the Related Art

Thrombopoietin (TPO), also referred to as c-Mpl ligand, mpl ligand, megapoietin, and megakaryocyte growth and development factor, is a glycoprotein that has been shown to be involved in production of platelets. See e.g., Wendling, F., et. al., Biotherapy 10 (4):269-77 (1998); Kuter D. J. et al., The Oncologist, 1:98-106 (1996); Metcalf, Nature 369: 519-520 (1994). TPO has been cloned and its amino acid sequence and the cDNA sequence encoding it have been described. See e.g., U.S. Pat. No. 5,766,581; Kuter, D. J. et al., Proc. Natl. Acad. Sci., 91:11104-11108 (1994); de Sauvage F. V., et al., Nature, 369: 533-538 (1994); Lok, S. et al., Nature 369:565-568 (1994); Wending, F. et al., Nature, 369: 571-574 (1994).

In certain instances, TPO activity results from binding of TPO to the TPO receptor (also called MPL). The TPO receptor has been cloned and its amino acid sequence has been described. See e.g., Vigon et al., Proc. Natl. Acad. Sci., 89:5640-5644 (1992).

In certain instances, TPO modulators may be useful in treating a variety of hematopoietic conditions, including, but not limited to, thrombocytopenia. See e.g., Baser et al. Blood 89:3118-3128 (1997); Fanucchi et al. New Engl. J. Med. 336:404-409 (1997). For example, patients undergoing certain chemotherapies, including but not limited to chemotherapy and/or radiation therapy for the treatment of cancer, or exposure to high levels of radiation may have reduced platelet levels. Treating such patients with a TPO agonist compound increases platelet levels. In certain instances, selective TPO modulators stimulate production of glial cells, which may result in repair of damaged nerve cells.

Generally, an increase in platelet count to a therapeutically beneficial level in a subject occurs after a prolonged period of time during a treatment regimen. For example, the increase in platelet count to a therapeutically beneficial level in a subject using a maintenance dose of a TPO modulator may occur after a week of treatment.

The standard dosing amount for the compound of the invention is generally considered to align with the amounts disclosed in International Application No. PCT/US07/074918, having an International filing date of Aug. 1, 2007; International Publication Number WO 2008/136843 and an International Publication date of Nov. 13, 2008, in which the highest dose prepared is a 100 mg tablet. However, the amounts described in PCT/US07/074918, specifically a 50 mg, 75 mg and 100 mg dose, were found to not meet the target platelet improvement counts in patients receiving carboplatin/paclitaxel as presented at the Multinational Association of Supportive Cancer Care—Annual Meeting, 2007 in a poster titled: *Efficacy and safety of eltrombopag, a novel, oral platelet growth factor on platelet counts in patients with cancer receiving carboplatin/paclitaxel chemotherapy*—by Baranwal et al.

It would be useful to provide a novel therapy which provides more effective and/or enhanced treatment using 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid or a pharmaceutically acceptable salt thereof.

SUMMARY OF THE INVENTION

One embodiment of this invention provides a method of treating thrombocytopenia in a human in need thereof which comprises the administration of a load dose of the compound 3'-[2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid, or a pharmaceutically acceptable salt thereof, suitably the bis-(monoethanolamine) salt, followed by the administration of a maintenance dose of the compound, or a pharmaceutically acceptable salt thereof, suitably the bis-(monoethanolamine) salt.

One embodiment of this invention provides a method of treating neutropenia in a human in need thereof which comprises the administration of a load dose of the compound 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid, or a pharmaceutically acceptable salt thereof, suitably the bis-(monoethanolamine) salt, followed by the administration of a maintenance dose of the compound, or a pharmaceutically acceptable salt thereof, suitably the bis-(monoethanolamine) salt.

One embodiment of this invention provides a method of increasing platelet production in a human in need thereof which comprises the administration of a load dose of the compound 3'-[(2Z)-[1-(3,4-dimethylphenyl)-1,5-dihydro-3- methyl-5-oxo-4H-pyrazol-4-ylidene]hydrazino]-2'-hydroxy-[1,1'-biphenyl]-3-carboxylic acid, or a pharmaceutically acceptable salt thereof, suitably the bis-(monoethanolamine) salt, followed by the administration of a maintenance dose of the compound, or a pharmaceutically acceptable salt thereof, suitably the bis-(monoethanolamine) salt.

One embodiment this invention provides a method for enhancing the number of peripheral blood stem cells obtained from a donor comprising administering to said donor a load dose of the compound 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid, or a pharmaceutically acceptable salt thereof, suitably the bis-(monoethanolamine) salt, followed by the administration of a maintenance dose of the compound, or a pharmaceutically acceptable salt thereof, suitably the bis-(monoethanolamine) salt, in an amount sufficient to enhance the number of peripheral blood stem cells prior to leukapheresis.

One embodiment of this invention provides a method of treating thrombocytopenia in a human in need thereof which comprises the administration of a high dose of the compound 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid, or a pharmaceutically acceptable salt thereof, suitably the bis-(monoethanolamine) salt.

One embodiment of this invention provides a method of treating neutropenia in a human in need thereof which comprises the administration of a high dose of the compound 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid, or a pharmaceutically acceptable salt thereof, suitably the bis-(monoethanolamine) salt.

One embodiment of this invention provides a method of increasing platelet production in a human in need thereof which comprises the administration of a high dose of the compound 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid, or a pharmaceutically acceptable salt thereof, suitably the bis-(monoethanolamine) salt.

One embodiment this invention provides a method for enhancing the number of peripheral blood stem cells obtained from a donor comprising administering to said donor a high dose of the compound 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid, or a pharmaceutically acceptable salt thereof, suitably the bis-(monoethanolamine) salt, in an amount sufficient to enhance the number of peripheral blood stem cells prior to leukapheresis.

DETAILED DESCRIPTION OF THE INVENTION

It is to be understood that both the foregoing general description and the following detailed description are exemplary and explanatory only and are not restrictive of the invention claimed.

Definitions

Unless specific definitions are provided, the nomenclatures utilized in connection with, and the laboratory procedures and techniques of, analytical chemistry, synthetic organic chemistry, and medicinal and pharmaceutical chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, pharmaceutical preparation, formulation, and delivery, and treatment of patients.

The term "TPO activity" refers to a biological activity that is known to result, either directly or indirectly from the presence of TPO. Exemplary TPO activities include, but are not limited to, proliferation and or differentiation of progenitor cells to produce platelets; hematopoiesis; growth and/or development of glial cells; repair of nerve cells; and alleviation of thrombocytopenia.

The term "thrombocytopenia" refers to a condition wherein the concentration of platelets in the blood of a patient is below what is considered normal for a healthy patient. In certain embodiments, thrombocytopenia is a platelet count less than 450,000, 400,000, 350,000, 300,000, 250,000, 200,000, 150,000, 140,000, 130,000, 120,000, 110,000, 100,000, 75,000, or 50,000 platelets per microliter of blood.

The term "loading dose" as used herein will be understood to mean a single dose or short duration regimen of Compound A or Compound B having a dosage higher than the maintenance dose administered to the subject to rapidly increase the blood concentration level of the drug. Suitably, a short duration regimen for use herein will be from: 1 to 14 days; suitably from 1 to 7 days; suitably from 1 to 3 days; suitably for three days; suitably for two days; suitably for one day. In some embodiments, the "loading dose" can increase the blood concentration of the drug to a therapeutically effective level. In some embodiments, the "loading dose" can increase the blood concentration of the drug to a therapeutically effective level in conjunction with a maintenance dose of the drug. The "loading dose" can be administered once per day, or more than once per day (e.g., up to 4 times per day).

The term "high dose" as used herein will be understood to mean a daily dosing regimen of Compound A or Compound B having a dosage higher than the maintenance dose administered to the subject to rapidly increase the blood concentration level of the drug when the subject is experiencing extreme thrombocytopenic situations. Such extreme thrombocytopenic situations can result from: treatment with therapeutic agents, such as chemotherapeutic agents; diseases, such as cancer and precancerous conditions; and organ failure, such as liver failure; and are, for example, when the attending doctor considers the subject is in danger of a catastrophic hemorrhage. In some embodiments, the "high dose" can increase the blood concentration of the drug to a therapeutically effective level. The "high dose" can be administered once per day in one dosage formulation, or in multiple dosage formulations more than once per day (e.g., up to 4 times per day). Suitably, as used herein, a "high dose" for use herein is an amount greater than the amounts disclosed in International Application No. PCT/US07/074918, having an International filing date of Aug. 1, 2007; International Publication Number WO 2008/136843 and an International Publication date of Nov. 13, 2008, in which the highest dose prepared is a 100 mg tablet, and not greater than about 400 mg.

The term "maintenance dose" as used herein will be understood to mean a dose that is serially administered (for example., at least twice), and which is intended to either slowly raise blood concentration levels of the compound to a therapeutically effective level, or to maintain such a therapeutically effective level. The maintenance dose is generally administered once per day and the daily dose of the maintenance dose is lower than the total daily dose of the loading dose.

Unless otherwise defined, in all dosing protocols described herein, the regimen of compound administered—whether a loading dose, high dose or maintenance dose regimen—does not have to commence with the start of treatment and terminate with the end of treatment, it is only required that the number of consecutive days in which the compound is administered, or the indicated dosing protocol, occur at some point during the course of treatment.

By the term "treating" and derivatives thereof as used herein, is meant therapeutic therapy. In reference to a particular condition, treating means: (1) to ameliorate or prevent the condition of one or more of the biological manifestations of the condition, (2) to interfere with (a) one or more points in the biological cascade that leads to or is responsible for the condition or (b) one or more of the biological manifestations of the condition, (3) to alleviate one or more of the symptoms, effects or side effects associated with the condition or treatment thereof, or (4) to slow the progression of the condition or one or more of the biological manifestations of the condition. Prophylactic therapy is also contemplated thereby. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof. Prophylactic therapy is appropriate, for example, when a subject is considered at high risk for developing thrombocytopenia such as because the subject was exposed to high levels of radiation, for example exposure to high levels of radiation due to a nuclear accident.

As used herein, the term "effective amount" and derivatives thereof means that amount of a drug or pharmaceutical agent that will elicit the biological or medical response of a tissue, system or human that is being sought, for instance, by a researcher or clinician. Furthermore, the term "therapeutically effective amount" and derivatives thereof means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The pharmaceutically acceptable salts of the compounds of the invention are readily prepared by those of skill in the art.

Compound A and Compound B are disclosed and claimed, along with pharmaceutically acceptable salts, hydrates, solvates and esters thereof, as being useful as agonists of the TPO receptor, particularly in enhancing platelet production and particularly in the treatment of thrombocytopenia, in International Application No. PCT/US01/16863, having an International filing date of May 24, 2001; International Publication Number WO 01/89457 and an International Publication date of Nov. 29, 2001, the entire disclosure of which is hereby incorporated by reference. Compound A and Compound B can be prepared as described in International Application No. PCT/US01/16863. The bis-(monoethanolamine) salt of Compound B (which is Compound A) is described in International Application No. PCT/US01/16863, is described in International Application No. PCT/US03/16255, having an International filing date of May 21, 2003; International Publication Number WO 03/098992 and an International Publication date of Dec. 4, 2003.

When referring to methods for administration, the term "co-administering" and derivatives thereof as used herein is meant either simultaneous administration or any manner of separate sequential administration of Compound A or Compound B, as described herein, and a further active agent or agents, as described herein. Preferably, if the administration is not simultaneous, the compounds are administered in a close time proximity to each other. Furthermore, it does not matter if the compounds are administered in the same dosage form, e.g. one compound may be administered topically and another compound may be administered orally.

TPO is known to have various effects including anti-apoptotic/survival effects on megakaryocytes, platelets and stem cells, and proliferative effects on stem cells and megakaryocytic cells (Kuter D. J. Seminars in Hematology, 2000, 37, 41-9). These TPO activities effectively increase the number of stem and progenitor cells so that there is synergistic effects when TPO is used in conjunction with other cytokines that induce differentiation.

Compound A and Compound B of the current invention are also useful in acting on cells for survival and/or proliferation in conjunction with other agents known to act on cells for survival and/or proliferation. Such other agents, or "further active ingredients" as used herein when referring to administration with Compound A or Compound B include but are not limited to: G-CSF, GM-CSF, TPO, M-CSF, EPO, Grobeta, IL-11, SCF, FLT3 ligand, LIF, IL-3, IL-6, IL-1, Progenipoietin, NESP, SD-01, or IL-5 or a biologically active derivative of any of the aforementioned agents, KT6352 (Shiotsu Y. et al., *Exp. Hemat.* 1998, 26, 1195-1201), uteroferrin (Laurenz J C., et al. *Comp. Biochem. & Phys., Part A. Physiology.*, 1997, 116, 369-77), FK23 (Hasegawa T., et al. *Int. J. Immunopharm.*, 1996, 18 103-112) and other molecules identified as having anti-apoptotic, survival or proliferative properties for stem cells, progenitor cells, or other cells expressing TPO Receptors.

As used herein Compound A and Compound B can be collectively referred to as "TPO modulator" or "TPO modulators".

As used throughout the specification and the claims all weights, amounts, indicated dosage quantities and the like, of Compound A and Compound B are indicated as the salt free or free acid amount. Further, it is understood that the compounds of the invention are generally administered in a pharmaceutical composition. The methods of the invention specifically include administration of Compound A and Compound B in pharmaceutical compositions in the specification and in the claims.

Treatment Regimens

In some embodiments, a loading dose of the TPO modulator can be administered to a subject to provide a therapeutic amount of Compound A or Compound B in the subject more rapidly than would occur by repeated smaller doses of said compounds for the treatment of thrombocytopenia or neutropenia.

Certain compounds that modulate TPO activity require a significant period of time to achieve a therapeutic effect. Accordingly the loading dose of the TPO modulator can be a multiple of the quantity of the selected compound administered per day as a maintenance dose of said compound. Further, the loading dose can be administered in increments form 1 to 4 times a day. For example, the total loading dose can be from about 2 times to about 8 times the quantity of the selected compound administered per day as a maintenance dose of said compound. The loading dose of Compound A or Compound B can be administered once a day or it can be divided into smaller portions and administered from 2 to about 4 times a day. Suitably, the loading dose can be administered in an amount ranging from about 50 mg to about 150 mg administered from 2 to 4 times in a day for from about 1 to 7 days, or in an amount ranging from about 200 mg to about 600 mg administered once a day for from about 1 to 7 days.

The amount of Compound A or Compound B administered in an individual loading dose can be from about 50 mg to about 600 mg, from about 50 mg to about 500 mg, or from about 100 mg to about 300 mg, in some embodiments the loading dose can be administered more than once a day. Suitably, the amount of Compound A or Compound B administered in an individual loading dose can be from about 50 mg to about 600 mg. For example, an individual loading dose can be 50 mg, 75 mg, 100 mg, 150 mg 200 mg, 300 mg, 400 mg, 500 mg or 600 mg of the TPO modulator.

The maintenance dose of Compound A, Compound B or pharmaceutically acceptable salts of Compound B administered is an amount from about 25 mg to about 150 mg once a day for at least two days, suitably for at least 5 days, suitably for at least 7 days, suitably for at least 14 days.

Some embodiments provide a method of increasing blood platelet counts in a subject comprising administering a loading dose of Compound A or Compound B followed by a maintenance dose regimen. In some embodiments, the blood platelet counts can increase from about 30% to about 40% from baseline, from about 40% to about 50% from baseline, from about 50% to about 60% from baseline, from about 60% to about 80% from baseline, from about 50% to about 60% from baseline, from about 60% to about 80% from baseline, from about 80% to about 100% from baseline, or from about 100% to about 150% from baseline based on administration of the loading dose regimen. For example, the blood platelet counts can increase from about 30% to about 150% from a reading of the blood platelet counts in the subject prior to treatment of a loading dose regimen with Compound A or Compound B.

Some embodiments provide a method of increasing blood platelet counts in a subject comprising administering a loading dose of Compound A or Compound B followed by a maintenance dose of Compound A or Compound B, respectively. In some embodiments, the amount of maintenance dose of Compound A or Compound B can be from about 25 mg to about 75 mg, from about 50 mg to about 100 mg, or from about 75 mg to about 150 mg administered per day.

In some embodiments, the amount of maintenance dose can be from about 25 mg to about 150 mg per day and the amount of loading dose can be from about 200 mg to about 600 mg per day. For example, the amount of maintenance dose can be from about 25 mg to about 100 mg per day and the amount of loading dose can be from about 200 mg to about 500 mg per day. Suitably, the amount of maintenance dose can be from about 25 mg to about 75 mg and the amount of loading dose can be from about 200 mg to about 400 mg per day.

Some embodiments provide a method of treating neutropenia in a subject comprising administering a loading dose of Compound A or Compound B followed by a maintenance dose of Compound A, Compound B or a pharmaceutically acceptable salt of Compound B, respectively. In some embodiments, the amount of maintenance dose of Compound A or Compound B can be from about 25 mg to about 150 mg, from about 25 mg to about 100 mg, or from about 50 mg to about 75 mg administered per day.

In some embodiments, a steady state blood plasma concentration can be reached within 24 hrs of administration of a single dose of a TPO modulator. For example, the steady state blood plasma concentration can be reached by administration of TPO modulator in an amount ranging from about 150 mg to about 600 mg, from about 200 mg to about 500 mg, from about 300 mg to about 450 mg, and from about 300 mg to about 600 mg.

In some embodiments, a steady state blood plasma concentration of a TPO modulator can be attained in a subject by using a loading dose of a TPO modulator and a subsequent maintenance dose of the TPO modulator. In some embodiments, the amount of the maintenance dose administered to the subject per day can be from about 10% to about 50% of the loading dose. Suitably, the amount of the maintenance dose administered to the subject per day can be from about 20% to about 50% of the loading dose. Suitably, the amount of the maintenance dose administered to the subject per day can be from about 25% to about 50% of the loading dose.

In some embodiments, a treatment regimen including a loading dose of a TPO modulator can increase the blood platelet count in a subject faster than a treatment regimen without a loading dose. For example, the loading dose of the TPO modulator can be administered to the subject on day one of the treatment regimen followed by administration of a maintenance dose during the remainder of the treatment regimen. In contrast, a treatment regimen can have a maintenance dose of a TPO modulator administered to the subject on day one and continued throughout the remainder of the treatment regimen. The treatment regimen with the loading dose of the TPO modulator can increase the blood platelet count faster than the treatment regimen without the loading dose. In a typical embodiment, the loading dose of the TPO modulator can be from about 2 times to about 6 times the quantity of the TPO modulator administered in the maintenance dose. For example, if the loading dose is 200 mg of the TPO modulator than the maintenance dose can range from about 25 mg to about 100 mg of the TPO modulator, if the loading dose is 300 mg of the TPO modulator than the maintenance dose can range from about 50 mg to about 150 mg of the TPO modulator, if the loading dose is 600 mg of the TPO modulator than the maintenance dose can range from about 75 mg to about 150 mg of the TPO modulator.

In some embodiments, the loading dose of the TPO modulator can be administered to the subject from 1 to 4 times in a 24 hour period, once every 24 hours, from 1 to 4 times in a 24 hour period for from 1 to 14 days, suitably form 1 to 7 days, followed by a maintenance does once a day for the course of treatment. Suitably the TPO modulator is administered once every 24 hours in an amount that can vary ranging from about 25 mg to about 600 mg.

The TPO modulator can be a multiple of the quantity of the selected compound administered per day as a maintenance dose of said compound.

In subjects experiencing extreme thrombocytopenic situations; a high dose of Compound A or Compound B can be administered to rapidly increase the blood concentration of the drug to a therapeutically effective level. Accordingly a high dose of Compound A or Compound B can be administered for at least 35 days, suitably for at least 21 days, suitably for at least 14 days, suitably for at least 10 days, suitably for at least 5 days, suitably for at least 2 days, suitably for at least 1 day; suitably for from 1 to 21 days.

Suitably, the amount of Compound A or Compound B administered as a high dose according to the present invention will be an amount selected from about 125 mg to about 400 mg; suitably, the amount will be selected from about 150 mg to about 375 mg; suitably, the amount will be selected from about 175 mg to about 350 mg; suitably, the amount will be selected from about 200 mg to about 300 mg; suitably, the amount will be 125 mg; suitably, the amount will be 150 mg; suitably, the amount will be 175 mg; suitably, the amount will be 200 mg; suitably, the amount will be 225 mg; suitably, the amount will be 250 mg; suitably, the amount will be 275 mg; suitably, the amount will be 300 mg; suitably, the amount will be 325 mg; the amount will be 350 mg; suitably, the amount will be 375 mg; suitably, the amount will be 400 mg. Accordingly, the amount of Compound A or Compound B administered as part of a high dose of the present invention will be an amount selected from about 125 mg to about 400 mg. For example, the amount of Compound A or Compound B administered as part of a high dose according to the present invention is suitably selected from 125 mg, 150 mg, 175 mg, 200 mg, 225 mg, 250 mg, 275 mg, 300 mg, 325 mg, 350 mg, 375 mg and 400 mg. Suitably, the selected amount of Compound A or Compound B is administered once a day, in one or more tablets.

Those skilled in the art can readily determine the efficacy of the present invention by comparing the claimed dosing protocol to a maintenance protocol, to a standard dosing amount, or to a placebo protocol in, for example, a clinical trial. An example of such a trial is described in an abstract presented at the American Society of Clinical Oncology (ASCO) meeting in June of 2010 (such abstracts were publicly available at least as of May 26, 2010). The abstract is titled: "An open-label, dose-ranging study to assess the safety, efficacy, and pharmacokinetics of eltrombopag in treating thrombocytopenia in patients with advanced sarcomas receiving doxorubicin and ifosfamide" by Chawla et al. the disclosure of which is incorporated by reference. Including a high dose protocol, or a load dose protocol prior to a maintenance protocol is useful, for example, when the subject has experienced or is expected to experience a dramatic decrease in platelet level or count such as when the subject has been exposed to high levels of radiation.

The compounds or combinations of the current invention are generally administered as pharmaceutical compositions or preparations readily known to those in the art such as described in International Application No. PCT/US07/074918, having an International filing date of Aug. 1, 2007; International Publication Number WO 2008/136843 and an International Publication date of Nov. 13, 2008, the entire disclosure of which is hereby incorporated by reference.

In one embodiment, the invention relates to a pharmaceutical composition containing Compound A or Compound B and a pharmaceutically acceptable carrier, wherein the amount of compound is selected from: about 125 mg to about 400 mg; suitably, about 150 mg to about 375 mg; suitably, about 175 mg to about 350 mg; suitably, about 200 mg to about 300 mg; suitably, 125 mg; suitably, 150 mg; suitably, 175 mg; suitably, 200 mg; suitably, 225 mg; suitably, 250 mg; suitably, 275 mg; suitably, 300 mg; suitably, 325 mg; suitably, 350 mg; suitably, 375 mg; suitably, 400 mg.

Optimal dosages of the presently invented compounds and combinations to be administered may be readily determined by those skilled in the art, and will vary with the particular compounds or combination in use, the strength of the preparation, the mode of administration, and the advancement of the disease condition. Additional factors depending on the particular patient being treated will result in a need to adjust dosages, including patient age, weight, diet, and time of administration.

The method of this invention of treating thrombocytopenia in humans comprises the in vivo administration to a subject in need thereof a therapeutically effective amount of a TPO modulator according to a dosing protocol of the present invention.

The method of this invention of treating neutropenia in humans comprises the in vivo administration to a subject in need thereof a therapeutically effective amount of a TPO modulator according to a dosing protocol of the present invention.

The method of this invention of enhancing the number of peripheral blood stem cells obtained from a donor comprises the in vivo administration to a subject in need thereof a therapeutically effective amount of a TPO modulator according to a dosing protocol of the present invention.

The method of this invention of enhancing platelet production in humans comprises the in vivo administration to a subject in need thereof a therapeutically effective amount of a TPO modulator according to a dosing protocol of the present invention.

The invention also provides for the use according to a dosing protocol of the present invention of a TPO modulator in the manufacture of a medicament for use in the treatment of thrombocytopenia in humans.

The invention also provides for the use of a TPO modulator in the manufacture of a medicament for use in therapy.

The invention also provides for a pharmaceutical composition for use according to a dosing protocol of the present invention in the treatment of thrombocytopenia which comprises a TPO modulator and a pharmaceutically acceptable carrier.

The invention also provides for the use according to a dosing protocol of the present invention a TPO modulator in the manufacture of a medicament for use in the treatment of thrombocytopenia.

The invention also provides for the use according to a dosing protocol of the present invention of a TPO modulator in the manufacture of a medicament or combination for use in therapy.

The invention also provides for a pharmaceutical composition for use, according to a dosing protocol of the present invention, in the treatment of thrombocytopenia which comprises a TPO modulator and a pharmaceutically acceptable carrier.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXPERIMENTAL DETAILS

Example 1

Capsule Composition

An oral dosage form for administering a compound of the present invention is produced by filing a standard two piece hard gelatin capsule with the ingredients in the proportions shown in Table I, below.

TABLE I

| INGREDIENTS | AMOUNTS |
| --- | --- |
| 3'-{N'-[1-(3,4-Dimethylphenyl)-3-methyl-5-oxo-1,5-dihydropyrazol-4-ylidene]hydrazino}-2'-hydroxybiphenyl-3-carboxylic acid | 125 mg |
| Mannitol | 155 mg |
| Talc | 16 mg |
| Magnesium Stearate | 4 mg |

Example 2

Injectable Parenteral Composition

An injectable form for administering a compound of the present invention is produced by stirring 1.5% by weight of 3'-{N'[1-(3,4-Dimethylphenyl)-3-methyl-5-oxo-1,5-dihydropyrazol-4-ylidene]hydrazino}-2'-hydroxybiphenyl-3-carboxylic acid bis-(monoethanolamine),
in 10% by volume propylene glycol in water.

Example 3

Tablet Composition

The sucrose, microcrystalline cellulose and a non-peptide TPO agonist, as shown in Table II below, are mixed and granulated in the proportions shown with a 10% gelatin solution. The wet granules are screened, dried, mixed with the starch, talc and stearic acid, then screened and compressed into a tablet.

TABLE II

| INGREDIENTS | AMOUNTS |
|---|---|
| 3'-{N'-[1-(3,4-Dimethylphenyl)-3-methyl-5-oxo-1,5-dihydropyrazol-4-ylidene]hydrazino}-2'-hydroxybiphenyl-3-carboxylic acid bis-(monoethanolamine) | 200 mg |
| Microcrystalline cellulose | 200 mg |
| sucrose | 40 mg |
| starch | 20 mg |
| talc | 10 mg |
| stearic acid | 5 mg |

While the preferred embodiments of the invention are illustrated by the above, it is to be understood that the invention is not limited to the precise instructions herein disclosed and that the right to all modifications coming within the scope of the following claims is reserved.

What is claimed is:

1. A method of treating thrombocytopenia in a human in need thereof which comprises administering a load dose of the compound 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid or a pharmaceutically acceptable salt thereof,
   wherein the load dose of the compound, or pharmaceutically acceptable salt thereof, is an amount ranging from about 50 mg to about 150 mg administered from 2 to 4 times in a day for 1 to 14 days, or is an amount ranging from about 200 mg to about 600 mg administered once a day for 1 to 14 days,
   followed by the administration of a maintenance dose of the compound, or pharmaceutically acceptable salt thereof,
   wherein the maintenance dose of the compound, or pharmaceutically acceptable salt thereof, is an amount of from about 25 mg to about 150 mg a day for at least two additional days.

2. The method of claim 1, wherein the compound is 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid bis-(monoethanolamine).

3. The method of claim 2, wherein the load dose for the compound is an amount ranging from about 200 mg to about 600 mg administered once a day for from 1 to 7 days.

4. The method of claim 3, wherein the maintenance dose of the compound is an amount of about 50 mg.

5. The method of claim 3, wherein the maintenance dose of the compound is an amount of about 75 mg.

6. The method of claim 3, wherein the maintenance dose of the compound is an amount of about 150 mg.

7. A method of increasing platelet production in a human in need thereof which comprises administering a load dose of the compound 3'-[(2Z)-[1-(3,4-di methyl phenyl)-1,5-dihydro-3-methyl-5-oxo-4H-pyrazol-4-ylidene]hydrazino]-2'-hydroxy-[1,1'-biphenyl]-3-carboxylic acid or a pharmaceutically acceptable salt thereof,
   wherein the load dose of the compound, or pharmaceutically acceptable salt thereof, is an amount ranging from about 50 mg to about 150 mg administered from 2 to 4 times in a day for 1 to 14 days, or is an amount ranging from about 200 mg to about 600 mg administered once a day for 1 to 14 days,
   followed by the administration of a maintenance dose of the compound, or pharmaceutically acceptable salt thereof,
   wherein the maintenance dose of the compound, or pharmaceutically acceptable salt thereof, is an amount of from about 25 mg to about 150 mg a day for at least two additional days.

8. The method of claim 7, wherein the compound is 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid bis-(monoethanolamine).

9. The method of claim 8, wherein the load dose for the compound is or is an amount ranging from about 200 mg to about 600 mg administered once a day for from 1 to 7 days.

10. The method of claim 9, wherein the maintenance dose of the compound is an amount of about 50 mg.

11. The method of claim 9, wherein the maintenance dose of the compound is an amount of about 75 mg.

12. The method of claim 9, wherein the maintenance dose of the compound is an amount of about 150 mg.

13. The method of claim 8, wherein the platelet production is increased prior to platelet pheresis, blood donation or platelet donation.

* * * * *